United States Patent [19]

Sundermeyer et al.

[11] Patent Number: 5,043,462

[45] Date of Patent: Aug. 27, 1991

[54] PROCESS FOR THE PRODUCTION OF GALLIUM-ALKYL COMPOUNDS

[75] Inventors: Wolfgang Sundermeyer, Neckargemund; Thomas Cymniak, Mannheim; Manfred Eschwey, Dusseldorf, all of Fed. Rep. of Germany

[73] Assignee: Messer Greisheim, Fed. Rep. of Germany

[21] Appl. No.: 516,099

[22] Filed: Apr. 27, 1990

[30] Foreign Application Priority Data

Apr. 28, 1989 [DE] Fed. Rep. of Germany ..... 39140568
Feb. 23, 1990 [DE] Fed. Rep. of Germany ..... 40057267

[51] Int. Cl.$^5$ .............................................. C07F 5/00
[52] U.S. Cl. ..................................................... 556/1
[58] Field of Search ........................................ 556/1

[56] References Cited

U.S. PATENT DOCUMENTS 4,604,473 8/1986 Cole-Hamilton et al. ............ 556/1
4,797,500 1/1989 Kadokura et al. .................... 556/1

FOREIGN PATENT DOCUMENTS 0130005 1/1985 European Pat. Off. ............... 556/1
1239687 11/1967 Fed. Rep. of Germany .
0231568 1/1986 German Democratic Rep. .
1301684 12/1989 Japan .................................. 556/1
 820146 9/1959 United Kingdom .
2123423 2/1984 United Kingdom ................. 556/1

OTHER PUBLICATIONS

John J. Eisch, "Organometallic Compounds of Group III. I. The Preparation of Gallium and Indium Alkyls from Organoaluminum Compounds", Journal of the American Chemical Society, vol. 84, No. 19, Oct. 17, 1962, pp. 3605-3610.

*Primary Examiner*—Arthur C. Prescott
*Assistant Examiner*—Porfirio Nazario-Gonzalez
*Attorney, Agent, or Firm*—Connolly & Hutz

[57] ABSTRACT

Gallium-alkyl compounds are produced, in that gallium-halogen compounds are reacted with alkyl aluminum halogenides in the presence of metal halogenides as auxiliary bases. Preference is given to the use of the corresponding chlorides and to the chlorides of the metals of groups I to III of the periodical table as auxiliary bases.

13 Claims, No Drawings

PROCESS FOR THE PRODUCTION OF GALLIUM-ALKYL COMPOUNDS

BACKGROUND OF DISCLOSURE

It is known that gallium-alkyl compounds, especially those with small alkyl radicals, play an important role in the production of III/V semiconductors, in particular those made of gallium arsenide and gallium phosphide, which are increasingly being used in the realms of electronics and solar technology. Up until now, the production of these gallium-alkyl compounds with the needed degree to purity and in the necessary amounts has posed tremendous difficulties.

Although it is known that gallium-halogen compounds can be alkylated by means of Grignard reagents, this entails a major disadvantage in that the only agent that can be used as the solvent, namely, ether, forms stable adducts with the gallium trialkyl produced. The separation of the adducts causes great problems and it is often accompanied by partial thermal decomposition and impurities in the desired gallium alkyls. The same problem arises in connection with a variant of the Grignard reaction, namely, the reaction of a (optionally metal-doped) magnesium-gallium alloy with alkyl halogenides. In the case of small alkyl radicals, alkylation with alkyl-lithium compounds or alkyl-sodium compounds can also only be carried out in the presence of these solvents which are disadvantageous because of their coordinating effect.

Even though the use of liquid metal alkyls circumvents the problems associated with the subsequent removal of the solvents, in this case, the reaction of gallium halogenides with trialkyl aluminum only allows for high yields if the amounts of this alkylating agent used are well above the stoichiometric level, while it is possible to make use of only one of the three alkyl groups. The reaction of dialkyl mercury for purposes of transferring alkyl groups. The reaction of dialkyl mercury for purposes of transferring alkyl groups to gallium, even with $HgCl_2$ catalysis, is extremely slow, and the extreme toxicity of dialkyl-mercury compounds prohibits a wider application range. Finally, the dialkyl-zinc compounds, which are also used for the alkylation of gallium-halogenide compounds, are difficult to obtain as initial products.

The known Wurtz synthesis of the simultaneous reaction of alkyl halogenides and metal halogenides in the presence of sodium is very poorly suited to produce gallium-alkyl compounds, not only because two alkyl groups react to form higher hydrocarbons and give rise to impurities, but primarily because the gallium-alkyl compounds, not only because two alkyl groups react to form higher hydrocarbons and give rise to impurities, but primarily because the gallium halogenides employed are reduced to gallium metal. The same also applies to reactions analogous to Wurtz's with halogen acceptor metals other than sodium such as, for example, metals of main groups I to III of the periodical table, which have already been studied as solvents in organic solvents and salt melts. Moreover, the latter are restricted to the methylation of just a few electropositive elements due to secondary reactions of higher alkyl halogenides. For the state of the art, reference is made to West German patent no. 1,239,687, East German patent no. 231,568 and British laid-open application no. 2,123,432.

SUMMARY OF INVENTION

The invention is based on the task of producing gallium-alkyl compounds, which are important for the manufacture of semiconductors—in particular short-chain gallium-alkyl compounds which are preferred for CVD processes due to the fact that they can be evaporated more easily—on the basis of inexpensive, easily available initial products, in a simple manner, in large amounts and with a high degree of purity.

DETAILED DESCRIPTION

In addition to the fact that they are difficult to obtain, when aluminum trialkyls react with gallium halogenides, only one of the three alkyl groups is transferred. The dialkyl aluminum halogenide which results as a by-product does not show any alkylating effect on gallium-halogen bonds, something which can be expected even less of alkyl aluminum dihalogenides. Surprisingly, it has turned out that alkyl aluminum dihalogenide actually is in a position to quantitatively transfer the alkyl groups to the gallium, in exchange for halogen atoms, if there is the addition of the cited auxiliary bases such as, for example, alkali metal halogenides and earth-alkali metal halogenides. Furthermore, even dialkyl aluminum halogenides and aluminum trialkyls as well as their mixtures with alkyl aluminum dichlorides (for instance, the technically available so-called alkyl aluminum sesquihalogenides, $R_3Al_2Cl_3$), can be employed under the same reaction conditions, optionally with the addition of aluminum halogenides for purposes of commuting these compounds and bringing about the vapor-pressure reduction associated with this. Preference is given to operating temperatures at which the mixture of the components is in the liquid state.

In addition to their technical availability, the use of, for example, alkyl aluminum sesquichlorides has the special advantage that the representatives with small alkyl groups are in the liquid state—and this is attained without having to deviate too much from normal conditions—thus making their handling, dosing, agitation, etc. very simple in the process according to the invention, a factor which is relevant in view of the fact that the reaction components are self-igniting. Since, due to their availability on an industrial scale, the chlorides are also the cheapest alternative among the auxiliary bases-—and this also applies to the commuting reagent, aluminum chloride—preference is given to the use of chlorides or mixtures thereof in the process according to the invention. Just the addition of the auxiliary base, sodium chloride, to the components dialkyl aluminum chloride or alkyl aluminum dichloride or mixtures thereof or else gallium trichloride results in a high yield of trialkyl gallium or dialkyl gallium chloride.

A further increase in the yield is achieved by adding potassium chloride as the auxiliary base, provided that one remains within the liquid range of the reaction mixture at the given reaction temperature.

Further special advantages of the process according to the invention in comparison to the processes known so far are the following: the process is carried out in the complete absence of solvents, so that no problems arise with respect to either separation or impurities. As a result, the space-time yield with respect to the volume of all of the reaction components is extraordinarily high. Whereas the synthesis products are (can be) removed in the form of vapor at the same time that there is a preliminary separation, it is possible to drain the mixture of by-products in the liquid form from the reactor and, optionally, to recover aluminum within the scope of the recycling methods according to the invention in order to produce alkyl aluminum halogenides. It is also particularly advantageous that the gallium employed for the production of the gallium trichloride to be used only has to have a low degree of purity (aluminum is the main source of impurities in the manufacturing process), since all of the undesired accompanying metals are to be found among the reaction by-products if the auxiliary bases are properly dosed, in other words, there is an additional purifying effect as a side effect. Moreover, should there still be gallium compounds contained in the by-product mixture after the reaction as a result of a not entirely quantitative reaction, the desired product, gallium, can easily be precipitated and recovered by adding aluminum metal (in the form of powder, chips, rods, granules). Finally, in the event of a device malfunction, it is possible to remove the reaction mixture in its liquid form, to cool it down to room temperature in order to convert it to the solid aggregate state, thus having it ready for disposal in a manner that is less hazardous than is possible with the synthesis in organic solvents.

In the process according to the invention, the only significant impurities that can occur in the final product are (alkyl)-aluminum-halogen compounds; nevertheless, it is easily possible to remove these compounds by means of rectification in a known manner by adding sodium fluoride during the final cleaning step which is necessary anyway for the gallium trialkyls which are important for the production of semiconductors.

The process according to the invention is illustrated in greater detail on the basis of the following embodiments.

EXAMPLE 1

A mixture of 250 g of $Me_3Al_2Cl_3$, 134 g of $AlCl_3$, 128 g of NaCl and 67 g of KCl is slowly heated in an atmosphere of inert gas until the mixture becomes completely liquid, while avoiding jumps in temperature and overheating. At a temperature between 110° C. and 120° C. (230° F. and 248° F.), 176 g of $GaCl_3$ are added and the mixture is heated to a temperature of 350° C. (662° F.) while being stirred for a period of time from 0.5 to 2 hours. In this process, 49 g of $Me_3Ga$ (42.7%) and 75 g of $Me_2GaCl$ (55.5%) are distilled. The reaction rate of gallium amounts to 98.2%.

EXAMPLE 2

A mixture of 205 g of $Me_3Al_2Cl_3$, 134 g of $AlCl_3$, 128 g of NaCl and 67 g of KCl is heated until the mixture becomes completely liquid. At a temperature between 110° C. and 120° C. (230° F. and 248° F.), 406 g of $Me_2GaCl$ are added and the mixture is further heated to a temperature of 350° C. (662° F.) while being stirred. In this process, 166 g of $Me_3Ga$ (48.2%) and 200 g of $Me_2GaCl$ (49.3%) are obtained, with the reaction rate of gallium amounting to 97.5%.

EXAMPLE 3

A mixture of 205 g of $Me_3Al_2Cl_3$, 134 g of $AlCl_3$, 128 g of NaCl and 67 g of KCl is heated until the mixture becomes completely liquid. At a temperature between 110° C. and 120° C. (230° F. and 248° F.), 202 g of $Me_2GaCl$ ate added and the mixture is heated to a temperature of 200° C. (392° F.). In this process, part of the products are already converted. At this temperature, 176 g of $GaCl_3$ are added and the mixture is then further heated to a temperature of 350° C. (662° F.). All in all, 114 g of $Me_3Ga$ and 201 g of $Me_2GaCl$ are obtained at a quantitative gallium reaction rate.

EXAMPLE 4

A total of 114 g of NaCl and 62 g of KCl are added to a mixture of 240 g of $GaCl_3$ and 280 g of $Me_3Al_2Cl_3$, and the resulting mixture is heated up to 350° C. (662° F.). This process yields 40 g of $Me_3Ga$ and 130 g of $Me_2GaCl$ (70.5%) with a gallium reaction rate of 96.1%.

EXAMPLE 5

A mixture consisting of 247 g of $Et_3Al_2Cl_3$, 134 g of $AlCl_3$ and 224 g of KCl is heated until it becomes completely liquid. At a temperature between 185° C. and 195° C. (365° F. and 383° F.), 176 g of $GaCl_3$ are added and the mixture is heated up to 350° C. (662° F.). This process yields 15.8 g of $Et_3Ga$ (10.1%) and 113 g of $Et_2GaCl$ (69.1%) with a gallium reaction rate of 79.2%.

EXAMPLE 6

A mixture consisting of 121 g of $Et_3Al_2Cl_3$, 65 g of $AlCl_3$ and 109 g of KCl is heated until it becomes completely liquid. At a temperature between 185° C. and 195° C. (365° F. and 383° F.), 239 g of $Et_2GaCl$ are added and the mixture is heated up to 350° C. (662° F). This process yields 110 g of $Et_3Ga$ (47.9%) and 118 g of $Et_2GaCl$ (49.4%) with a gallium reaction rate of 97.3%.

EXAMPLE 7

A total of 149 g of KCl are added to a mixture consisting of 114 g of $Et_3Al_2Cl_3$, 133 g of $AlCl_3$ and 176 g of $GaCl_3$, and the resulting mixture is heated up to 350° C. (662° F.). This process yields 33 g of $Et_3Ga$ (21%) and 118 g of $Et_2GaCl$ (72%) with a gallium reaction rate of 93%.

What is claimed:

1. In a process for the production of gallium-alkyl compounds wherein a gallium compound is reacted with an alkyl compound, the improvement being in that a gallium-halogen compound is reacted with an alkyl aluminum halogenide in the presence of at least one metal halogenide as auxiliary bases, and the reaction being solvent-free in the liquid range of the reaction mixture.

2. Process according to claim 1, characterized in that the gallium-halogen compound is selected from the group consisting of gallium trihalogenides, alkyl gallium dihalogenides and dialkyl gallium halogenides.

3. Process according to claim 2, characterized in that the gallium-halogen compound is gallium chloride.

4. Process according to claim 1, characterized in that the alkyl aluminum halogenide is selected from the group consisting of dialkyl aluminum halogenides, alkyl aluminum dihalogenides or mixtures of alkyl aluminum halogenides with dialkyl aluminum halogenides or sesquihalogenides ($R_3Al_2X_3$).

5. Process according to claim 4, characterized in that the gallium-halogen compound is gallium chloride.

6. Process according to claim 1, characterized in that the halogenides of the metals of groups I to III of the periodical table of elements are used as auxiliary bases.

7. Process according to claim 6, characterized in that the gallium-halogen compound is gallium chloride.

8. Process according to claim 1, characterized in that the auxiliary bases are selected from the group consisting of sodium chloride and potassium chloride and mixtures thereof.

9. Process according to one of claims 1 through 8, characterized in that the reaction is carried out at temperatures between 70° C. and 450° C. (158° F. and 842° F.).

10. Process according to claim 1, characterized in that trimethyl gallium is produced by the process.

11. Process according to claim 1, characterized in that Me$_2$GaCl is produced by the process.

12. Process according to claim 1, characterized in that the alkyl aluminum halogenide is sesquichloride.

13. In a process for the production of gallium-alkyl compounds wherein a gallium compound is reacted with an alkyl compound, the improvement being in that a gallium-halogen compound is reacted with trialkyl aluminum with the addition of aluminum halogenide.

* * * * *